United States Patent

(12) United States Patent
Chao

(10) Patent No.: US 9,975,931 B2
(45) Date of Patent: May 22, 2018

(54) USE OF AN IMMUNOMODULATORY PROTEIN FROM *GANODERMA* IN PROMOTING NEURITE OUTGROWTH

(71) Applicant: Mycomagic Biotechnology Co., Ltd., New Taipei (TW)

(72) Inventor: Ming-Wei Chao, Chung-Li (TW)

(73) Assignee: MYCOMAGIC BIOTECHNOLOGY CO., LTD., New Taipei (TW)

( * ) Notice: Subject to any disclaimer, the term of this patent is extended or adjusted under 35 U.S.C. 154(b) by 0 days. days.

(21) Appl. No.: 14/918,132

(22) Filed: Oct. 20, 2015

(65) Prior Publication Data

US 2016/0115208 A1 Apr. 28, 2016

Related U.S. Application Data

(60) Provisional application No. 62/065,884, filed on Oct. 20, 2014.

(51) Int. Cl.
*C07K 14/37* (2006.01)
*C07K 14/375* (2006.01)
*A61K 45/06* (2006.01)
*A61K 38/00* (2006.01)
*A61K 38/16* (2006.01)

(52) U.S. Cl.
CPC .......... *C07K 14/375* (2013.01); *A61K 38/168* (2013.01); *A61K 45/06* (2013.01)

(58) Field of Classification Search
None
See application file for complete search history.

(56) References Cited

U.S. PATENT DOCUMENTS

| 6,207,639 | B1 | 3/2001 | Blaschuk et al. |
| 7,601,808 | B2 * | 10/2009 | Lin ..................... C07K 14/375 530/350 |
| 7,846,438 | B2 | 12/2010 | Mi et al. |
| 8,476,238 | B2 * | 7/2013 | Ko ..................... A61K 31/517 424/649 |
| 8,481,711 | B2 | 7/2013 | Kaminishi et al. |
| 2009/0005340 | A1 * | 1/2009 | Kristiansen ............ C12P 19/04 514/54 |

OTHER PUBLICATIONS

Seow et al, (BMC Complementary and alternative med 13: Jul. 2013—abstract).*
Zhou et al (Acta physiologica Sinica, 62: 547-554, 2010—abstract).*
Guo et al (Acta Anatomica Sinica 37: 509-513, 2006—abstract).*
Halliday et al Clin Exp Pharmacol Physiol 27: 1-8, 200.*
Steece-Collier et al., PNAS USA 99(22): 13972-13974, 2002.*
Feigin et al., Curr Opin Neurol 15: 483-489, 2002.*
Cheng et al, Jiepou Xuebao 38: 27-33, 2007—abstract only.*
Xie et al Chinese J Neurol 38: 355-358, 2005—abstract only.*
What is Ganoderma spore, pp. 1-4, downloaded on Jan. 9, 2018 <http://www.allife.com.au/faq/what-is-ganoderma-spore>.*
Boh et al. (2007) "Ganoderma lucidum and its pharmaceutically active compounds," Biotechnol. Annu. Rev. 13:265-301.
Hsu et al. (1997) "Fip-vvo, a new fungal immunomodulatory protein isolated from Volvariella volvacea," Biochem. J. 323(Pt 2):557-565.
Jinn et al. (2006) "Functional Expression of FIP-gts, a Fungal Immunomodulatory Protein from Ganoderma Tsugae in Sf21 Insect Cells," Biosci. Biotechnol. Biochem. 70:2627-2634.
Ko et al. (1995) "A New Fungal Immunomodulatory Protein, FIP-fve Isolated from the Edible Mushroom, Flammulina velutipes and its Complete Amino Acid Sequence," Eur. J. Biochem. 228:244-249.
Liao et al. (2006) "Transcriptionally mediated inhibition of telomerase of fungal immunomodulatory protein from Ganoderma tsugae in A549 human lung adenocarcinoma cell line," Mol. Carcinog. 45:220-229.
Liao et al. (2008) "Induction of premature senescence in human lung cancer by fungal immunomodulatory protein from Ganoderma tsugae," Food Chem. Toxicol. 46:1851-1859.
Xuanwei et al. (2008) "Identification of medicinal *Ganoderma* species based on PCR with specific primers and PCR-RFLP," Planta Med. 74:197-200.

* cited by examiner

*Primary Examiner* — Daniel E Kolker
*Assistant Examiner* — Aditi Dutt
(74) *Attorney, Agent, or Firm* — Lathrop Gage LLP; James H. Velema, Esq.

(57) ABSTRACT

The inventors surprisingly found that an immunomodulatory protein from *Ganoderma* can promote neurite outgrowth, suggesting that the immunomodulatory protein from *Ganoderma* can treat and/or prevent neurological disorders. Accordingly, the invention provides a method for promoting neurite outgrowth, the method comprising exposing the neuron to an effective amount of an immunomodulatory protein derived from *Ganoderma*, or a recombinant or a composition thereof. The invention also provides a method for treating and/or preventing a neurological disorder, the method comprising administering an effective amount of an immunomodulatory protein derived from *Ganoderma*, or a recombinant or a composition thereof to a subject.

5 Claims, 6 Drawing Sheets

SEQUENCE LISTING

<160> NUMBER OF SEQ ID NOS: 4

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum -continued

```
<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30

Phe Ile Asp Thr Val Thr Phe Pro Thr Val Leu Thr Asp Lys Ala Tyr
            35                  40                  45

Thr Tyr Arg Val Val Val Ser Gly Lys Asp Leu Gly Val Arg Pro Ser
        50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
                100                 105                 110

<210> SEQ ID NO 4
<211> LENGTH: 140
<212> TYPE: PRT
<213> ORGANISM: Ganoderma microsporum

<400> SEQUENCE: 4

Glu Ala Glu Ala Glu Phe Met Ser Asp Thr Ala Leu Ile Phe Thr Leu
1               5                   10                  15

Ala Trp Asn Val Lys Gln Leu Ala Phe Asp Tyr Thr Pro Asn Trp Gly
            20                  25                  30

Arg Gly Arg Pro Ser Ser Phe Ile Asp Thr Val Thr Phe Pro Thr Val
            35                  40                  45

Leu Thr Asp Lys Ala Tyr Thr Tyr Arg Val Val Val Ser Gly Lys Asp
        50                  55                  60

Leu Gly Val Arg Pro Ser Tyr Ala Val Glu Ser Asp Gly Ser Gln Lys
65                  70                  75                  80

Ile Asn Phe Leu Glu Tyr Asn Ser Gly Tyr Gly Ile Ala Asp Thr Asn
                85                  90                  95

Thr Ile Gln Val Tyr Val Ile Asp Pro Asp Thr Gly Asn Asn Phe Ile
                100                 105                 110

Val Ala Gln Trp Asn Tyr Leu Glu Gln Lys Leu Ile Ser Glu Glu Asp
            115                 120                 125

Leu Asn Ser Ala Val Asp His His His His His
        130                 135                 140
```

USE OF AN IMMUNOMODULATORY PROTEIN FROM *GANODERMA* IN PROMOTING NEURITE OUTGROWTH

RELATED APPLICATIONS

This application claims priority to U.S. Provisional Application Ser. No. 62/065,884, filed Oct. 20, 2014, the content of which is incorporated herein by reference in its entirety.

SEQUENCE LISTING

The instant application contains a Sequence Listing which has been submitted electronically in ASCII format and is hereby incorporated by reference in its entirety. Said ASCII copy is named 574947_LLB_009_ST25.txt and is 2,961 bytes in size.

FIELD OF THE INVENTION

The present invention relates to a new use of an immunomodulatory protein derived from *Ganoderma* or a recombinant or a composition thereof in promoting neurite outgrowth and treating and/or preventing neurological disorders. Particularly, the immunomodulatory protein is derived from *Ganoderma microsporum*.

BACKGROUND OF THE INVENTION

Once a neural circuit network is damaged by brain injury or spinal cord injury and the network is thereby cut off or results in nerve cell death, the physiological and/or motor functions governed by nerves are lost, and it becomes extremely difficult to restore the neural circuit. Neurites are often packed with microtubule bundles, the growth of which is stimulated by Nerve Growth Factor (NGF), as well as tau proteins, MAP1, and MAP2. U.S. Pat. No. 6,207,639 provides methods for enhancing and/or directing neurite outgrowth, comprising contacting a neuron with a cell adhesion modulating agent, wherein the modulating agent enhances cadherin-mediated cell adhesion. U.S. Pat. No. 7,846,438 discloses contacting a neuron (such as a CNS neuron) with an effective amount of an agent that modulates TAJ complex formation and/or signaling to modulate growth and/or survival of a neuron. U.S. Pat. No. 8,481,711 provides a non-peptidic nerve axon and/or neurite outgrowth agent for allowing a nerve axon and a neurite to elongate.

Many therapeutic effects have been reported of Lingzhi species, such as immunomodulatory, anti-tumor, hepatoprotective, antioxidant, and cholesterol-lowering effects (Jinn et al., 2006, *Biosci Biotechnol Biochem*, 70, 2627-2634). All of these therapeutic effects are attributed to triterpenoids, polysaccharides, and glycoproteins (Boh et al., 2007, *Biotechnol Annu Rev*, 13, 265-301; Jinn et al., 2006, *Biosci Biotechnol Biochem*, 70, 2627-2634). A new glycoprotein class in Lingzhi named fungal immunomodulatory proteins (FIPs) was recently identified. So far, at least 4 FIPs have been isolated and purified from *Ganoderma lucidum*, LZ-8, (*G. lucidum*), FIP-gts (*Ganoderma tsugae*), and FIP-gja (*Ganoderma sinensis*) (Hsu et al., 1997, *Biochem J*, 323 (Pt 2), 557-565; Ko et al., 1995, *Eur J Biochem*, 228, 244-249; Xuanwei et al., 2008, *Planta Med*, 74, 197-200). According to a previous study, FIP-gts from *G. tsugae*, a popular chemopreventive mushroom in Asia, has anti-cancer function and is involved in the regulation of hTERT/telomerase expression (Liao et al., 2006, *Mol Carcinog*, 45, 220-229). In addition, FIP-gts inhibits the growth of A549 cancer cells, leading to cell cycle arrest, consequently inducing premature cellular senescence in lung cancer cells. Moreover, FIP-gts results in significant inhibition of tumor growth in athymic nude mice implanted with A549 cells (Liao et al., 2008, *Food Chem Toxicol*, 46, 1851-1859). US 20100009915 provides a method for suppressing proliferation of a cancer cell and a method for suppressing a tumor cell mobility, comprising providing to the tumor cell a purified polypeptide of a fungal immunomodulatory protein, LZ-8. U.S. Pat. No. 7,601,808 discloses an immunomodulatory protein cloned from *Ganoderma microsporum* and this protein has immunomodulator efficiency.

However, no prior art discloses, teaches or suggests that immunomodulatory proteins from *Ganoderma* are relevant to neurite outgrowth.

SUMMARY OF THE INVENTION

The invention provides a method for promoting neurite outgrowth, the method comprising exposing the neuron to an effective amount of an immunomodulatory protein derived from *Ganoderma*, or a recombinant or a composition thereof, thereby promoting neurite outgrowth. Particularly, the immunomodulatory protein from *Ganoderma*, or a recombinant thereof can promote the outgrowth of axons and dendrites.

The invention also provides a method for treating and/or preventing a neurological disorder, the method comprising administering an effective amount of an immunomodulatory protein derived from *Ganoderma*, or a recombinant or a composition thereof to a subject thereby treating and/or preventing a neurological disorder.

In one embodiment, the immunomodulatory protein is derived from *Ganoderma lucidum, Ganoderma tsugae, Ganoderma microsporum* or *Ganoderma sinensis*. Preferably, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis* or a recombinant thereof. Preferably, the immunomodulatory protein is derived from *Ganoderma microsporum* (GMI) or a recombinant thereof (reGMI). More preferably, the reGMI has the amino acid sequence as shown in SEQ ID NO: 1 and SEQ ID NO: 2, SEQ ID NO:3 or SEQ ID NO:4.

In one embodiment, the immunomodulatory protein from *Ganoderma*, or a recombinant or a composition thereof, are therefore useful in the therapy of, for example, disorders of the nervous system, conditions of the nervous system that are secondary to a disease, condition, or therapy having a primary effect outside of the nervous system, injuries to the nervous system caused by physical, mechanical, or chemical trauma, memory loss, or psychiatric disorders. In another embodiment, the method of the invention can be used in the treatment of peripheral nerve damage caused by physical injury (associated with, e.g., burns, wounds, surgery, and accidents), ischemia, prolonged exposure to cold temperature (e.g., frost-bite), damage to the central nervous system due to, for example, stroke or intracranial hemorrhage (such as cerebral hemorrhage), dementia, Alzheimer's disease, Huntington's disease or Parkinson's disease.

In another embodiment, immunomodulatory protein from *Ganoderma*, or a recombinant thereof can be combined with a neurite outgrowth agent for combination therapy in promoting neurite outgrowth or treating and/or preventing a neurological disorder.

BRIEF DESCRIPTION OF THE DRAWING

FIG. 4A, Group 1: immature neuron, post-treatment; FIG. 4B, Group 2: immature neuron, pre-treatment; FIG. 4C, Group 3: mature neuron, post-treatment; and FIG. 4D, Group 4: mature neuron, pre-treatment. For statistical analysis, each experiment was performed in triplicate and repeated 3 times. The results were expressed as means±SD for three independent experiments, and analyzed the differences between the groups by using Student t-tests with GraphPad statistics software. $*p<0.05$, $p<0.01$ and $*p<0.001$ compared with the controls indicate significant differences.

DETAILED DESCRIPTION OF THE INVENTION

Figure 1:
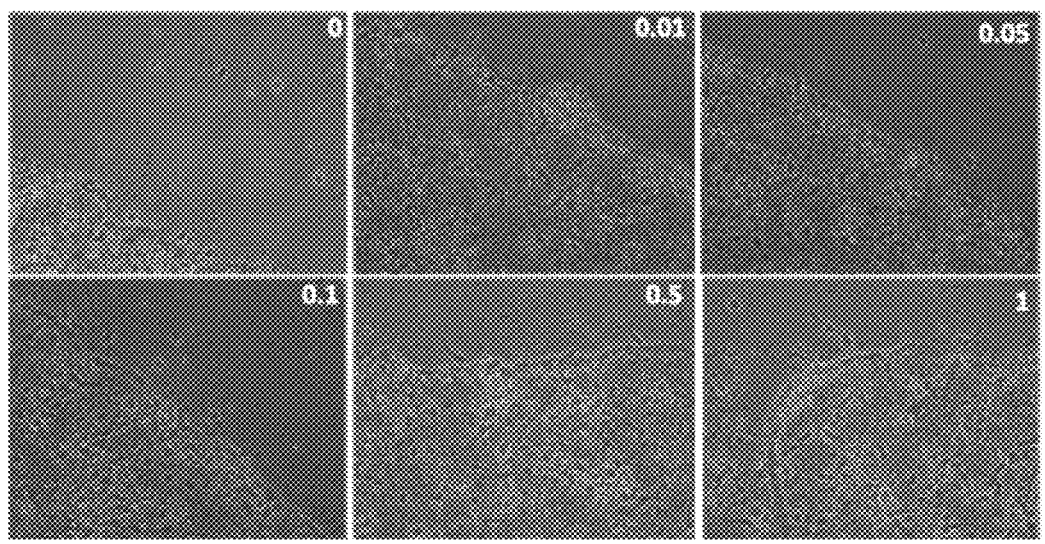
FIG. 1 shows the treatment with recomGMI in different concentration and scrape at immature neurons (Group 1: Treat and scrape at same time).

The inventors surprisingly found that an immunomodulatory protein from *Ganoderma* can promote neurite outgrowth, suggesting that the immunomodulatory protein from *Ganoderma* can treat and/or prevent neurological disorders.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are orated herein by reference.

In this application, the use of the singuincorplar includes the plural, the article "a" or "an" means "at least one", and the use of "or" means "and/or", unless specifically stated otherwise.

In this application, the word "comprise," or variations such as "comprises" or "comprising," indicate the inclusion of any recited integer or group of integers but not the exclusion of any other integer or group of integers in the specified method, structure, or composition.

As used herein, the term "neuron" includes a neuron and a portion or portions thereof (e.g., the neuron cell body, an axon, or a dendrite). The term "neuron" denotes nervous system cells that include a central cell body or soma and two types of extensions or projections: dendrites, by which, in general, the majority of neuronal signals are conveyed to the cell body, and axons, by which, in general, the majority of neuronal signals are conveyed from the cell body to effector cells, such as target neurons or muscle.

The term neurite as used herein encompasses all such cell processes (including both axon and dendrite) growing out of a neuron.

The term "neurite outgrowth" refers to the process of cells growing out of a neuron, or to the cells comprising an outgrowth from a neuron.

As used herein, "neurological disorders" means any physiological dysfunction or death of neurons present in the central nervous system or peripheral nervous system or caused by glia cell dysfunction. A non-limited list of such disorders comprises multiple sclerosis, sciatic nerve defect, brain or code injury, dementia, frontotemporal lobe dementia, Alzheimer's disease, Parkinson's disease, Huntington's disease, prion diseases, neuronopathies and motor neuron disorders. "Neuronopathies" are characterized by neuronal cell death of motor neurons or sensory neurons, and hence neuronopathies can be subdivided into motor and sensory neuron disorders.

As used herein, "promote" or "increase", or "promoting" or "increasing" are used interchangeably herein. These terms refer to the increase in a measured parameter in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit", "prevent" or "reduce," or "inhibiting", "preventing" or "reducing" are used interchangeably herein. These terms refer to the decrease in a measured parameter in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is As used herein, "treatment" or "treating" or "ameliorating" are used interchangeably herein. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, "therapeutically effective amount" means an amount sufficient to treat a subject afflicted with a disease or to alleviate a symptom or a complication associated with the disease.

As used herein, "subject" refers to either a human or non-human animal.

In one aspect, the invention provides a method for promoting neurite outgrowth, the method comprising exposing the neuron to an effective amount of an immunomodulatory protein derived from *Ganoderma*, or a recombinant or a composition thereof, thereby promoting neurite outgrowth. The immunomodulatory protein from *Ganoderma*, or a recombinant thereof of the present disclosure can be used to promote neurite outgrowth. Particularly, the immunomodulatory protein from *Ganoderma*, or a recombinant thereof can promote the outgrowth of axons and dendrites. By exposing the neurons to the effective amount of the immunomodulatory protein from *Ganoderma*, or a recombinant thereof, the axons and dendrites increase in length and density and recover by regeneration.

In one embodiment, the immunomodulatory protein or a recombinant thereof is derived from *Ganoderma lucidum*, *Ganoderma tsugae*, *Ganoderma microsporum* or *Ganoderma sinensis*. Preferably, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis* or a recombinant thereof.

In one embodiment, the immunomodulatory protein is derived from *Ganoderma microsporum* (GMI) or a recombinant thereof (reGMI). More preferably, the immunomodulatory protein (GMI or reGMI) has the amino acid sequence: (1) -Leu-Ala-Trp-Asn-Val-Lys-(LAWNVK; SEQ ID NO:1) and (2) -Asp-Leu-Gly-Val-Arg-Pro-Ser-Tyr-Ala-Val-(DLGVRPSYAV; SEQ ID NO:2), or the amino acid sequence of: MSDTALIFTLAWNVKQLAFDYTPNWGRGRPSSFIDT-VTFPTVLTDKAYTYRVVVSGKD LGVRPSYAVESDG-SQKINFLEYNSGYGIADTNTIQVYVIDPDTGNN-FIVAQWN (SEQ ID NO:3) or the amino acid sequence of EAEAEFMSDTALIFTLAWNVKQLAFDYTPNWGR-GRPSSFIDTVTFPTVLTDKAYTYRVV VSGKDL-GVRPSYAVESDGSQKINFLEYNSGY-GIADTNTIQVYVIDPDTGNNFIVAQWNY LEQKLISEEDLNSAVDHHHHHH (SEQ ID NO:4).

In one embodiment, the amount for promotion of neurite outgrowth ranges from about 0.65 μg to about 650 μg weight of the immunomodulatory protein per kg body weight. Amounts between about 0.65 μg to about 6.5 μg, about 6.5 μg to about 65 μg, about 65 μg to about 650 μg of the immunomodulatory protein per kg body weight are more preferred; more preferably, about 6.5 μg to about 325 μg of the immunomodulatory protein per kg body weight.

In another aspect, the invention provides a method for treating and/or preventing a neurological disorder, the method comprising administering an effective amount of an immunomodulatory protein derived from *Ganoderma*, or a recombinant or a composition thereof to a subject thereby treating and/or preventing a neurological disorder. The immunomodulatory protein from *Ganoderma*, or a recombinant or a composition thereof of the present disclosure can be used to treat and/or prevent neurological disorder. The immunomodulatory protein from *Ganoderma*, or a recombinant or a composition thereof are therefore useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) memory loss, and (v) psychiatric disorders. Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson-plus syndromes (e.g., multiple system atrophy, progressive supranuclear palsy, and corticobasal degeneration), dementia, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

In addition, the methods of the invention can be used in the treatment of nerve damage, such as peripheral neuropathy. The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, for example, stroke or intracranial hemorrhage (such as cerebral hemorrhage).

In one embodiment, the immunomodulatory protein or a recombinant thereof is derived from *Ganoderma lucidum*, *Ganoderma tsugae*, *Ganoderma microsporum* or *Ganoderma sinensis*. Preferably, the immunomodulatory protein is LZ-8 derived from *Ganoderma lucidum*, FIP-gts derived from *Ganoderma tsugae*, GMI derived from *Ganoderma microsporum*, or FIP-gja derived from *Ganoderma sinensis* or a recombinant thereof.

In one embodiment, the immunomodulatory protein is derived from *Ganoderma microsporum* (GMI) or a recombinant thereof (reGMI). More preferably, the immunomodulatory protein (GMI or reGMI) has the amino acid sequence: (1) -Leu-Ala-Trp-Asn-Val-Lys-(LAWNVK; SEQ ID NO:1) and (2) -Asp-Leu-Gly-Val-Arg-Pro-Ser-Tyr-Ala-Val-(DLGVRPSYAV; SEQ ID NO:2), or the amino acid sequence of: MSDTALIFTLAWNVKQLAFDYTPNWGRGRPSSFIDT-VTFPTVLTDKAYTYRVVVSGKD LGVRPSYAVESDG-SQKINFLEYNSGYGIADTNTIQVYVIDPDTGNN-FIVAQWN (SEQ ID NO:3), or the amino acid sequence of EAEAEFMSDTALIFTLAWNVKQLAFDYTPNWGR-GRPSSFIDTVTFPTVLTDKAYTYRVV VSGKDL-GVRPSYAVESDGSQKINFLEYNSGY-GIADTNTIQVYVIDPDTGNNFIVAQWNY LEQKLISEEDLNSAVDHHHHHH (SEQ ID NO:4).

The immunomodulatory protein or a recombinant thereof of the invention can be administered to a patient either alone or in pharmaceutical compositions where it is mixed with suitable carriers and excipients. The immunomodulatory protein or a recombinant thereof or a composition of the invention can be administered parenterally, such as by intravenous injection or infusion, intraperitoneal injection, subcutaneous injection, or intramuscular injection. The immunomodulatory protein or a recombinant thereof or a composition can be administered orally or rectally through appropriate formulation with carriers and excipients to form tablets, pills, capsules, liquids, gels, syrups, slurries, suspensions and the like. The immunomodulatory protein or a recombinant thereof or a composition can be administered topically, such as by skin patch. The immunomodulatory protein or a recombinant thereof or a composition can be formulated into topical creams, skin or mucosal patch, liquids or gels suitable to topical application to skin or mucosal membrane surfaces. The immunomodulatory protein or a recombinant thereof or a composition can be administered by inhaler to the respiratory tract for local or systemic treatment of cancers.

In one embodiment, the amount of the immunomodulatory protein or a recombinant thereof for administration may range from about 0.65 µg to about 650 µg weight of the immunomodulatory protein per kg body weight. Amounts between about 0.65 µg to about 6.5 µg, about 6.5 µg to about 65 µg, about 65 µg to about 650 µg of the immunomodulatory protein per kg body weight are more preferred; more preferably, about 6.5 µg to about 325 µg of the immunomodulatory protein per kg body weight.

The dosage of the immunomodulatory protein or a recombinant thereof or a composition suitable for use according to the present invention can be determined by those skilled in the art on the basis of the disclosure herein. The medicament will contain an effective dosage depending upon the route of administration and pharmacokinetics of the active agent. Suitable pharmaceutical carriers and excipients are those suitable for the particular route of administration of the formulation (i.e., oral, parenteral, topical or by inhalation). Immunomodulatory protein or a recombinant thereof is mixed into the pharmaceutical composition by means of mixing, dissolving, granulating, dragee-making, emulsifying, encapsulating, entrapping or lyophilizing processes. The pharmaceutical compositions for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

In another embodiment, the immunomodulatory protein or a recombinant thereof can be combined with a neurite outgrowth agent for combination therapy in promoting neurite outgrowth or treating and/or preventing a neurological disorder. The immunomodulatory protein or a recombinant thereof also can be combined with a neurite outgrowth agent as a pharmaceutical composition. That is, the invention provides a pharmaceutical composition comprising the immunomodulatory protein or a recombinant thereof and an additional neurite outgrowth agent, wherein the composition can promote neurite outgrowth or treat and/or prevent a neurological disorder. In one embodiment, the neurite outgrowth agent is a nicotinamide adenine dinucleotide (NAD) analogue; a neurotrophic factor containing a 5-acyl-2-amino-1,3-selenazole analogue; a neurotrophic factor containing ebselen; a neurite outgrowth agent containing at least one compound selected from the group consisting of coffeic acid and a derivative thereof; a neurite outgrowth agent containing at least one plant extract selected from the group consisting of rosemary and sage that contain carnosic acid; a cell death-suppressing substance containing lysophosphatidylethanolamine; a neurite outgrowth composition containing a cell organelle alkalinization agent such as monensin or concanamycin A; a neurite outgrowth agent containing polyalkoxyflavonoid such as nobiletin or tangeretin; a neurite outgrowth activator containing a glycosaminoglycan derivative; a neurite outgrowth agent containing a lactacystin derivative; a neurite outgrowth agent containing a small molecule heterocyclic ketone or thioester compound; a neurite outgrowth agent containing derivatives of ganglioside and N-acyl-N-lyso-ganglioside, N'-acyl-N'-lyso-ganglioside, and N,N'-di- or poly-acyl-N,N'-dilyso-ganglioside; a neurite outgrowth agent comprising a chondroitin sulfate/dermatan sulfate hybrid chain containing a disaccharide of GlcUA(2S)-GalNAc(4S) (B unit); a neurite outgrowth inducer containing a sugar chain having a bisecting GlcNAc, a complex carbohydrate having the aforementioned sugar chain in the structure thereof, a derivative of the aforementioned sugar chain, etc.; a neurite outgrowth inducer containing, as an active ingredient, a low-molecular-weight synthetic compound; Tctex-1-related polypeptide; TAJ polypeptide; or neural cell adhesion molecule.

Without further elaboration, it is believed that one skilled in the art can utilize the present invention to its fullest extent on the basis of the preceding description. The following examples are, therefore, to be construed as merely illustrative and not a limitation of the scope of the present invention in any way.

EXAMPLE

Example 1

Neurite Regeneration Assay

Figure 3:
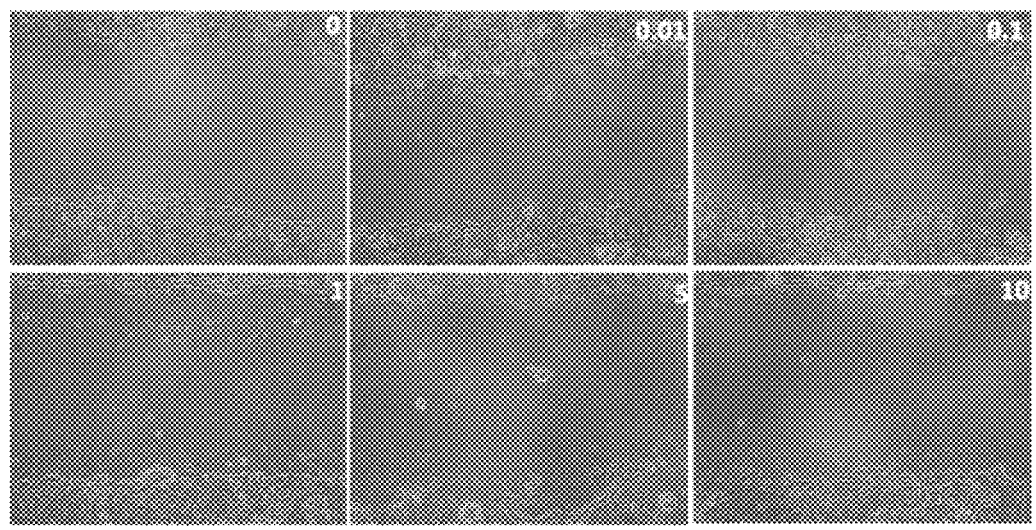
FIG. 3 shows the treatment with recomGMI in different concentration at DIV15 and scrape at DIV17 (Group 4: PreTreat 48 h and scrape later).

The recombinant immunomodulatory protein derived from *Ganoderma microsporum* (hereafter referred to as "recomGMI") was manufactured by Mycomagic Biotechnology Co., Ltd., according to the method described in U.S. Pat. No. 7,601,808 and has an amino acid sequence shown in FIG. 3B of U.S. Pat. No. 7,601,808.

Neuronal cultures were prepared from hippocampi or cortices of rat embryos of both sexes at 18 days of gestation as described previously (Firestein B L, Bredt D S (1998), *J Neurochem* 71:1846-1853; Tseng C Y, Firestein B L (2011), *J Neurosci* 31:15468-15480). Hippocampi were dissociated, and cells were plated on 6-well plates coated with poly-D-lysine at a density of $6 \times 10^5$ cells/well. Neurons were cultured in Neurobasal media supplemented with B27, penicillin, streptomycin, and GlutaMax (Invitrogen).

To test the neurite regeneration in vitro, wound healing assays were processed, which were used for testing cell migration and neurite outgrowth in previous reports (Loh S H, Francescut L, Lingor P, Bahr M, Nicotera P (2008), *Cell Death Differ* 15:283-298; Wu C L, Chou Y H, Chan Tseng C Y, Firestein B L (2011) *J Neurosci* 31:15468-15480g; Y J, Teng N Y, Hsu H L, Chen L (2012) *PLoS One* 7:e34999). The tests were separated into four groups: Group 1: immature neuron, post-treatment; Group 2: immature neuron, pre-treatment; Group 3: mature neuron, post-treatment; and Group 4: mature neuron, pre-treatment. All the treatments were administered for 24 h. Mature neuron is the culture neuron in D.I.V 17 to 21, which is fully matured and formed synaptic connections with other cells. It represents the largest population of cells in the adult brain. Immature neuron indicates the culture neuron in D.I.V 10 to 12, which has developed neurites but no spine-mediated synaptic connection. It stands for potential neuronal progenitor cells in the specific area of brain, such as subventricular zone. In Groups 1 and 3, different concentrations of recomGMI are used along with scraping wound, while Groups 2 and 4 groups are pre-treated with different concentrations of recomGMI 48 h before wounds are made. The wound is made by P1000 tips and defined as healing day 0.

Figure 2:
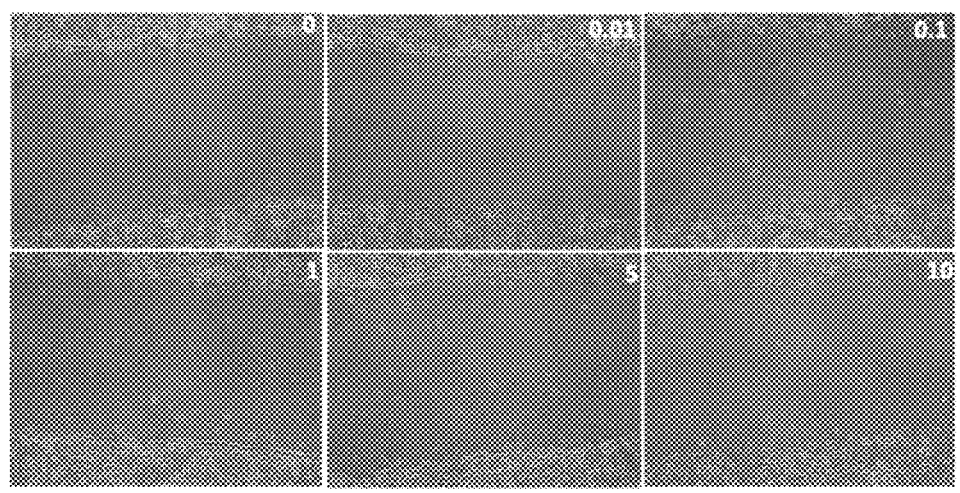
FIG. 2 shows the treatment with recomGMI in different concentration at DIV8 and scrape at immature neurons (Group 2: PreTreat 48 h and scrape later).
Figure 4A:
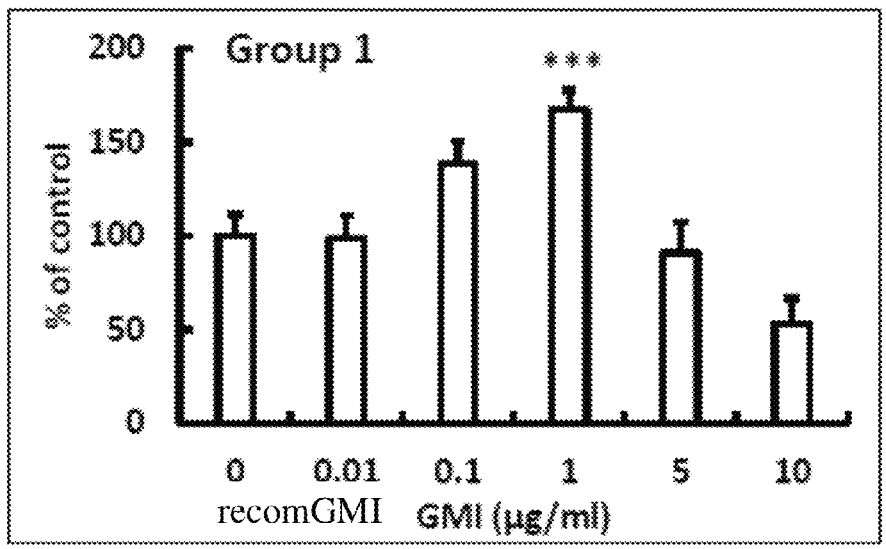
FIGS. 4A-4D show that the distance of neurite outgrowth was measured after injury and recomGMI treatment.
Figure 4B:
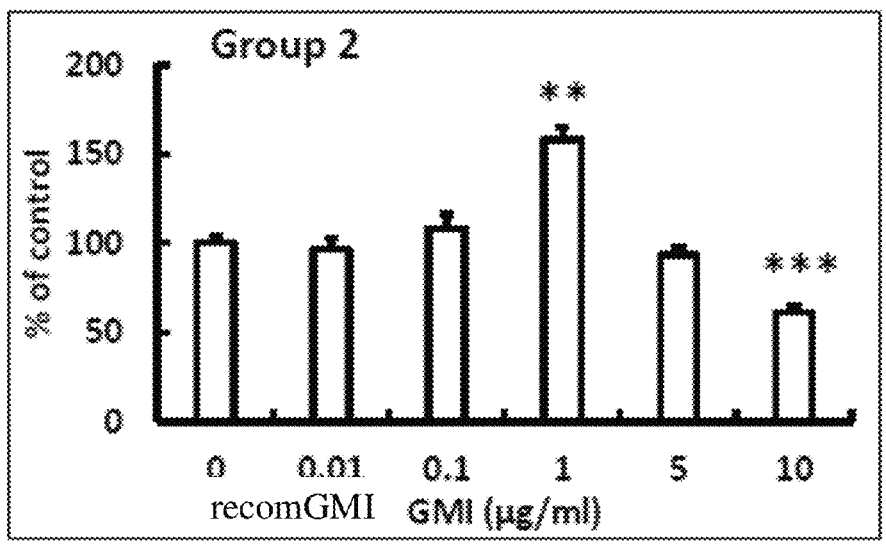

The results show that 1 µg/ml recomGMI has the obvious effects on promoting neurite regeneration both in Groups 1 and 2 (FIG. 1 and FIG. 2). As shown in FIG. 4A and FIG.

Figure 4C:
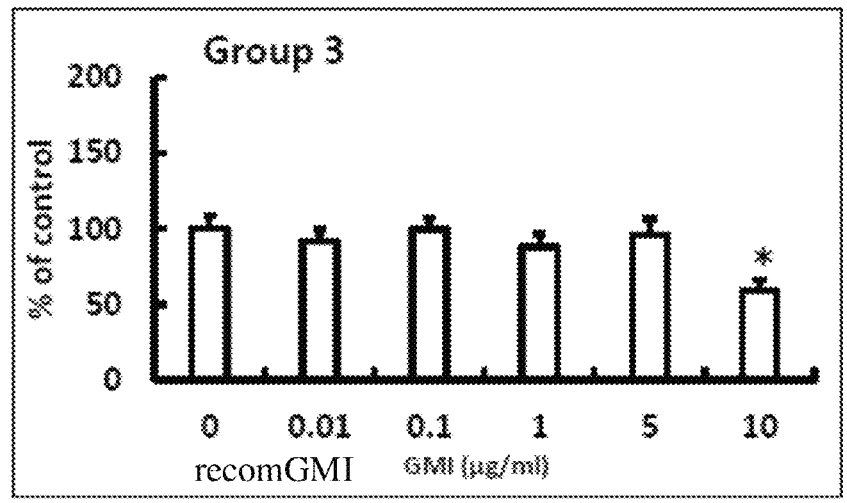
Figure 4D:
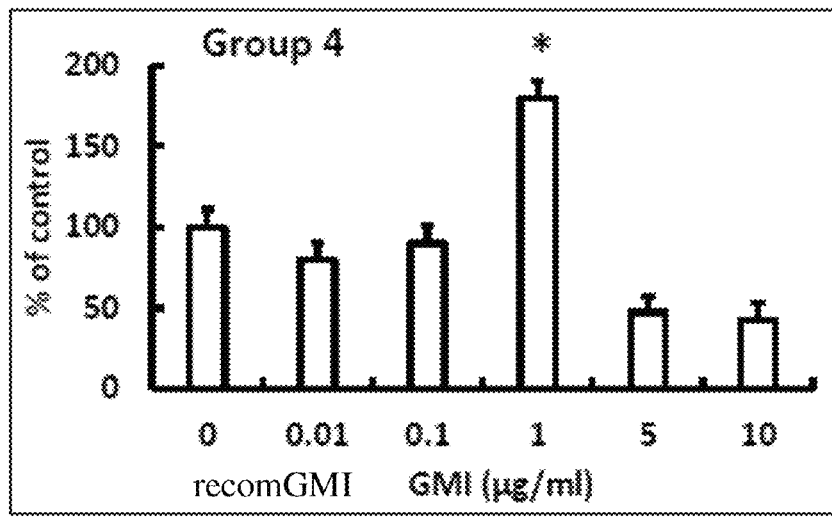

4B, we measured the outgrowth of the neurite regeneration and the quantitation results suggest the average neurite distance reach 140% and 170% of the control respectively at Group 1 treated with recomGMI 0.1 µg/ml and recomGMI 1 µg/ml. The neurites in Group 2 also can regenerate up to 160% at recomGMI 1 µg/ml. Hence, both pre-treatment and co-treatment of recomGMI could ameliorate neurite outgrowth after injury. However, comparing Groups 3 and 4 (FIG. 3), in matured neurons, pre-treatment of recomGMI (<1 µg/ml) enhance the regeneration of neurite after injury but not in co-treated group (FIG. 4C, data not shown in image). Quantitation data suggest neurite outgrowth can reach 180% in Group 4 (FIG. 4D). However, the higher dose of recomGMI (5 and 10 µg/ml) is toxic to both mature and immature neurons.

Example 2

Morris Water Maze Task Assay

The Morris water maze (MWM) is a test of spatial learning for rodents that relies on distal cues to navigate from start locations around the perimeter of an open swimming arena to locate a submerged escape platform. The water maze method was performed as described in D'Hooge, R; De Deyn, P P (August 2001), "*Applications of the Morris water maze in the study of learning and memory*". Brain Research. Brain Research Reviews 36 (1): 60-90 with modifications.

A plastic black circular pool 160 cm in diameter and 45 cm in height was filled with water (25+/−2° C.) to a depth of 27 cm. A circular platform (12 cm in diameter) was placed at a specific location from the edge of the pool and submerged 2-3 cm below the water surface. For spatial learning, animals were subjected to 4 trials per day; each trial was conducted for 1 minute. The training procedure lasted 4 days, and a total of 16 trials were given. For these trials, the rats were positioned at different starting points spaced equally around the perimeter of the pool in random order. They had 60 s to find the hidden platform. If a rat could not find the platform, it was guided to the platform and was allowed to remain there for 20 s. The time each animal took to reach the platform was recorded as the escape latency. A probe trial of 60 s was given on day 5 to test their memory retention. The rats were placed in the pool with the platform removed, and the time they spent in quadrant 5 was recorded. Quadrant 5 is the target quadrant. For the trained and swimming control experiments, rats in the trained group were subjected to the regular water maze learning procedure.

After the water maze training procedure, three groups of S. D. rats (pretreat groups) were orally administered 0.33 µg/kg recomGMI (pretreat low dose), 3.3 µg/kg recomGMI (pretreat middle dose) and 33 µg/kg recomGMI (pretreat high dose), respectively for one month. The three groups of rats were subjected to brain injury surgery. After the surgery, the rates were continuously administered 0.33 µg/kg recomGMI, 3.3 µg/kg recomGMI and 33 µg/kg recomGMI, respectively for one month. After the first four days, the rats were subject to water maze training procedure for 5 days.

Other three groups of S. D. rats were directly subjected to brain injury surgery without administration of recomGMI. After the surgery, the three groups of rats were orally administered 0.33 µg/kg recomGMI (post-treat low dose), 3.3 µg/kg recomGMI (post-treat middle dose) and 33 µg/kg recomGMI (post-treat high dose), respectively for one month. After the first four days, the rats were subject to water maze training procedure for 5 days.

Figure 5:
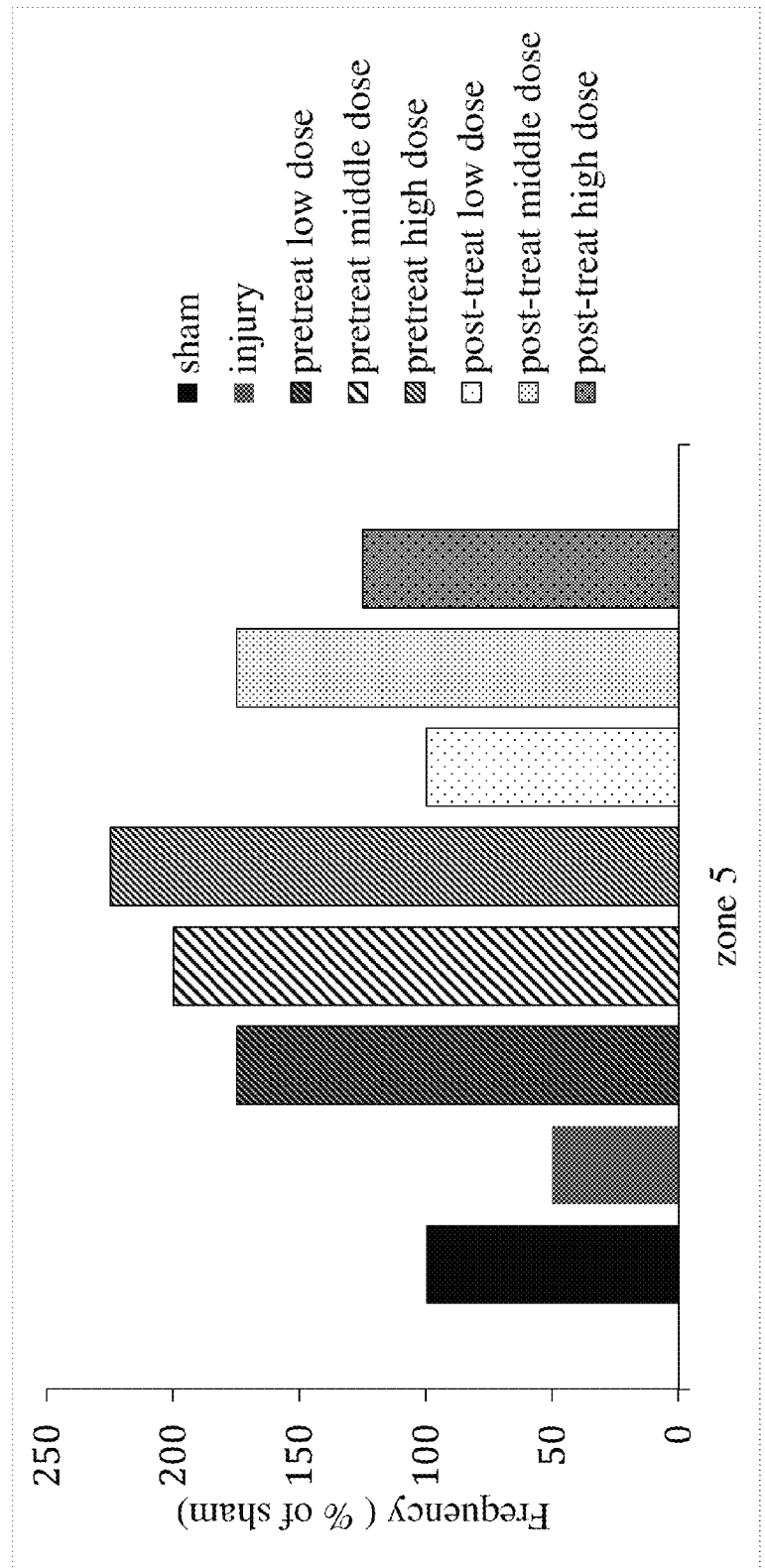
FIG. 5 shows the animal model results of the treatment with recomGMI in Morris water maze task assay.

After the conclusion of recomGMI administration, the six groups of rats were subjected to the water maze assay. As shown in FIG. 5, the treatment efficacy in the pretreat groups exhibits a dose-dependent manner and the post-treat middle dose group exhibits an advantageous effect in comparison with the sham group.

What is claimed is:

1. A method for improving memory or promoting neurite regeneration in a subject in need thereof, the method comprising administering an effective amount of an immunomodulatory protein derived from *Ganoderma microsporum* (GMI), or its recombinant (reGMI) or a composition thereof, to the subject, wherein the immunomodulatory protein, the recombinant, or the composition thereof, comprises the amino acid sequence of SEQ ID NO:3.

2. The method of claim 1, wherein the subject is suffering from a neurological disorder.

3. The method of claim 2, wherein the neurological disorder is ischemia, dementia, Alzheimer's disease, Huntington's disease or Parkinson's disease.

4. The method of claim 1, wherein the effective amount of an immunomodulatory protein derived from *Ganoderma*, or a recombinant or a composition thereof, is from about 0.65 μg to about 650 μg per kg body weight.

5. The method of claim 1, wherein immunomodulatory protein derived from *Ganoderma*, or a recombinant or a composition thereof, is in combination with an additional neurite outgrowth agent.

* * * * *